United States Patent
Laabs et al.

[11] Patent Number: 5,964,733
[45] Date of Patent: Oct. 12, 1999

[54] SUCTION DEVICE FOR MEDICAL PURPOSES

[76] Inventors: Walter Laabs, Oestringer Strasse 64; Hans-Gunter Appel, Auenweg 2, both of DE-26419 Schortens, Germany

[21] Appl. No.: 09/091,455
[22] PCT Filed: Dec. 7, 1996
[86] PCT No.: PCT/EP96/05488
 § 371 Date: Dec. 21, 1998
 § 102(e) Date: Dec. 21, 1998
[87] PCT Pub. No.: WO97/21454
 PCT Pub. Date: Jun. 19, 1997

[30] Foreign Application Priority Data

Dec. 14, 1995 [DE] Germany .......................... 195 46 640

[51] Int. Cl.⁶ .................................................. A61M 1/00
[52] U.S. Cl. .............................. 604/119; 604/35; 604/902
[58] Field of Search ............................ 604/119, 35, 118, 604/129, 902, 244, 247; 606/123

[56] References Cited

U.S. PATENT DOCUMENTS 5,542,929 8/1996 Laabs et al. ........................... 604/119

Primary Examiner—John D. Yasko
Attorney, Agent, or Firm—Pillsbury Madison & Sutro LLP

[57] ABSTRACT

The invention relates to a suction device for medical purposes with one or more side apertures and with a valve which responds to a vacuum. The invention is characterised in that the side apertures are covered by film halves which overlap in the middle, one of said halves being made from highly elastic thin material while the other is made from a stiff inflexible material and covers the flexible film in the overlap region. The side apertures can also take the form of elongated apertures. An advantage of this embodiment is the low damage to tissue when used in the overpressure area especially in minimally invasive surgical applications.

6 Claims, 1 Drawing Sheet

SUCTION DEVICE FOR MEDICAL PURPOSES

This application is the national phase of international application PCT/EP96/05488 filed Dec. 7, 1996 which designated the U.S.

The invention relates to a suction device for medical purposes particularly suitable for usage in Minimal Invasive Surgery (MIS).

In surgery, extravasating blood, tissue liquids, tissue fragments, bone fragments and -dust as well as pus, but also rinsing liquid such as sodium chloride solution or Ringer solution have to be removed from the region under treatment. While in the past mull swabs were used, these days suction devices are engaged. In dentistry e.g., salvia, blood, and left-overs from drilling have to be succed off. In intensive surgery, anesthesia, and endoscopic examination, body liquids of a variety of viscosities and consistencies have to be succed off (e.g., mucus, blood, urine, stool, bile, gastric juice, etc., also contrast liquids).

In general, suction devices for medical purposes consist of a permanently installed or a mobile vacuum pump, which is connected to a low pressure collecting containe that in turn, via an over-flow prevention apparatus, is connected to a so-called secretion bottle which in turn is connected to the suction tip via a suction tube. Both small volume and large volume suction apparatus exist, where such devices are denoted large volume suction apparatus whose inner diameter is larger than 4.9 mm. These suction apparatus can be plastic, but they can also be made from metal, or from other material.

When, while sucking off, tissue completely covers the aperture of the suction tip of the suction apparatus, low pressure is established, which can touch on the order of the pump's low pressure of 0.1 bar. Thus, tissue is pressed into the sucking aperture by the air pressure so that traumatic damage can be inflicted onto the tissue. In addition, tissue can be vered off at the inner edge of the sucking aperture, which likewise can lead to injuries.

Suction devices for medical purposes are known already. The DE-PS 40 04 373 describes suction devices for medical purposes consisting of a suction aparatus made from metal or plastics, which is equipped with one or several side apertures with a low pressure valve. According to the patent, the side apertures are shaped as elongated holes or as continuous grooves and they are covered with thin slitted film or slittable film respectively which can either be mounted as a tube or which can be pasted as film strips. In this way it can be avoided, even at a low pumping pressure, close to 0.1 bar, that the suction tip sucks fast to the tissue. So-called traumatic tissue defects do not occur any more. Moreover, optimal adaptation of the sucking power to the individual circumstances can be achieved by varying the slit size. Thus, at the same time, vacuum control in the way of manual, temporary coverage of the side apertures at the suction tip, considered disturbing during surgery, is rendered superfluous. As opposed to suction apparatus which are equipped in a common way, with side apertures above the suction tip, suction devices according to DE 40 02 373 can be operated without disturbing noise.

Although suction devices known according to the state of the art, meanwhile, largely help to avoid to traumatic tissue injuries as well as disturbing operating noises, and, in particular, are successfully used in neuro surgery, their range of service is constructionally limited to such operations that take place at atmospheric pressure. However, it can be observed that the number of operations, frequently conducted at high pressure of 0.01 to 0.1 bar (above atmospheric pressure), such as e.g. in the field of minimal invasive surgery, is steadily increasing. Due to rapid progress of medical technology as well as of opto electronics Minimal Invasive Surgery gathers importance. Concerning MIS, the healing process can be accelerated and the duration of the usually cost intensive stationary treatment can be reduced considerably since both, the operation expenditure can be kept at low levels, and the actual surgical treatment can be reduced to a minimum. In particular, given the socio-political importance of cost-reducing measures in the health-care system, the reduction of the stationary treatment's duration is likely to foster MIS operation techniques and applications.

Minimal Invasive Surgery, as well, requires the removal of blood and rinsing liquid by a suction device during surgical treatment. In order to avoid traumatic injuries of tissue as a consequence of the suction tip's sucking fast, the advantageous features of a suction device according to DE 40 02 373 should not be relinquished in Minimal Invasive Surgery. MIS treatment is generally conducted at high pressure of 0.01 to 0.1 bar. Since the side apertures of the suction device, in order to function according to the patent, are positioned outside the body i.e., in a region of normal pressure, one would risk the loss of pressure gas, in the case of the slitted film according to DE 40 02 373, whenever the suction device is not operating.

Hence, there is yet demand for suction devices that can be used also to work at high pressure and which in this case, in particular, can be used in MIS treatment, while not simultaneously giving rise to traumatic injuries of tissue and to undesired background noise, and which, in addition, are of simple design and, when necessary, are easily cleaned and sterilized. Scope of the invention is therefore to maintain the advantages of DE 40 02 373 in the case of operations conducted at high pressure, and in particular in the case of such operations as Minimal-Invasive-Surgery.

According to the invention, suction devices with one suction aparatus made of plastics or metal are now proposed which are equipped with one or several side apertures with a low pressure valve and which are characterized in that the side apertures are covered by concentrically overlapping film halves of which one consists of highly elastic thin material while the other is made from rigid inflexible material. The elasticity of both materials is important whereas the strength of the films is not of major importance. For this reason equally strong films may be used. Furthermore, crucial with regards to the invention is that the rigid film covers the flexible film in the overlap region. It is advantegous if the film strips each cover more than half of the aperture from the opposite sides respectively. The rectilinear film strips can be affixed to the surface of the suction tip such that the overlapping edges of the film run parallel to each other and the overlap region, in the case of elongated holes, runs along the middle axis.

The side apertures can be shaped as elongated holes and usually they are positioned at a large distance to the suction tip. Thus, the valves surely can stay outside the body i.e., in the region of normal pressure while the suction tip is immersed into the high pressure region.

In this way, critically low pressure leading to traumatic tissue injuries is surely avoided. At the same time the closure of the suction tube is assured by pressing the flexible film strip against the inelastic film strip when high pressure builds up inside the suction tube. Any leakage of pressure gas does not occur. Hence, steady operation conditions are ensured and the suction aparatus can remain continuously inside the operation region. The suction tip, from the outside, neither needs to be moved to nor removed from the operation region according to the needs and necessities.

A discription of the invention using the drawings is given below:

Figure 1:
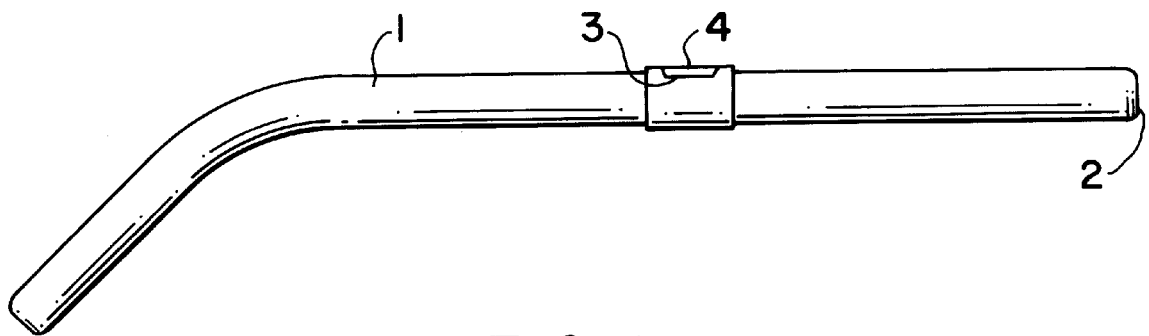
FIG. 1 shows a side view of a suction aparatus according to the invention.
Figure 2:
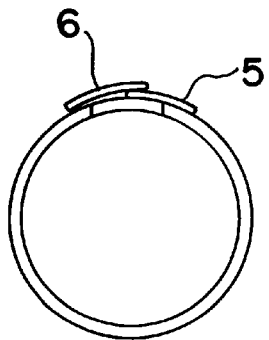
FIG. 2 shows a cross-sectional view of the same suction aparatus where high pressure is applied inside the suction tube.
Figure 3:
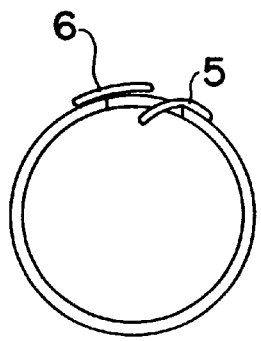
FIG. 3 shows a cross-sectional view of the same suction aparatus where a pressure is applied inside the suction tube which is less than a critical low pressure.
Figure 4:
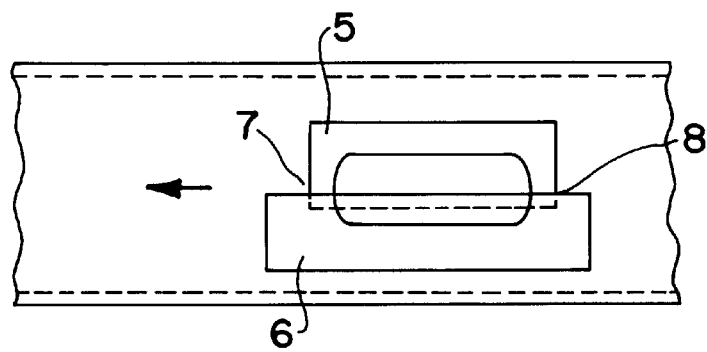
FIG. 4 shows an elongated hole covered with foil strips seen from above.

The suction aparatus (1) is equipped with an aperture (2) and one or several elongated holes (3) which in turn are covered by films overlapping in the middle where one of the films (5) is made from flexible material, while the other (6) is made from rigid material. The films (5, 6) are arranged in such a fashion that in the overlap region the rigid film (6) covers the flexible film (5). Seen from above (FIG. 4) it becomes obvious that the overlapping film edges (7) and (8) run parallel to the longitudinal axis of the elongated hole, the film edges each cover slightly more than between one half and up to approximately ⅔ of the surface of the elongated hole and that the overlap region is positioned approximately in the region of the longitudinal axis of the elongated hole. The utilized films advantageously consist of flexible or rigid plastic film materials respectively and can easily be affixed to the suction tube.

We claim:

1. Suction device for medical purposes, suitable to be used in Micro-Invasive-Surgery (MIS), with at least one suction opening as well as one or several side apertures where the side apertures are each equipped with a low pressure valve, characterized in that the side apertures are covered with film halves which overlap in the middle where one of said film halves consists of highly elastic thin material and the other consists of rigid inflexible material where the rigid film covers the flexible film in the overlap region.

2. The suction device according to claim 1, wherein the side apertures are shaped as elongated holes.

3. The suction device according to claim 1, wherein the side apertures are located in a region of normal pressure.

4. The suction device according to claim 1, wherein the flexible and the rigid films each cover more than half of the hole's surface from the opposite sides respectively.

5. The suction device according to claim 1, wherein the overlapping film edges run parallel to each other.

6. The suction device according to claim 1, wherein the films are plastics.

* * * * *